United States Patent [19]
Ackermann et al.

[11] Patent Number: 5,373,543
[45] Date of Patent: Dec. 13, 1994

[54] COMPUTER TOMOGRAPHY APPARATUS HAVING MEANS FOR PRODUCING A SHADOWGRAPH

[75] Inventors: Rudolf Ackermann, Buckenhof; Reinhard Rueckriem, Erlangen, both of Germany

[73] Assignee: Siemens Aktiengesellschaft, Munich, Germany

[21] Appl. No.: 70,202

[22] Filed: Jun. 2, 1993

[30] Foreign Application Priority Data

Jun. 5, 1992 [DE] Germany ............................ 4218637

[51] Int. Cl.$^5$ ............................................. A61B 6/03
[52] U.S. Cl. ............................................ 378/20; 378/8; 378/98.12
[58] Field of Search ..................... 378/4, 8, 10, 11, 14, 378/20, 62, 98.12

[56] References Cited

U.S. PATENT DOCUMENTS 4,216,526  8/1980  Karwoski .
4,352,986 10/1982  Pfeiler .
4,791,934 12/1988  Brunnett .......................... 378/20
5,247,556  9/1993  Eckert et al. .

FOREIGN PATENT DOCUMENTS 2939975  4/1981  Germany .
4103588  5/1992  Germany .

OTHER PUBLICATIONS

"A 3-D Display with a Linearly Moving Mirror to Reflect a Series of 2-D Cross Sections and Its Application to Noninvasive Angiography," Yamanaka et al., IEEE Trans. on Med. Imag., vol. 7, No 3 (Sep., 1988), pp. 193-197.

Primary Examiner—David P. Porta
Attorney, Agent, or Firm—Hill, Steadman & Simpson

[57] ABSTRACT

A computer tomography system, in addition to conducting a standard computer tomography scan, is capable of producing a shadowgraph prior to conducting the computer tomography examination with the measurement unit in a locked position, as well as one or more real time shadowgraphs during the computer tomography examination. The shadowgraph obtained with the measurement unit in the lock position can then be superimposed with one or more of the real time shadowgraphs obtained during the tomography examination, and the superimposed image displayed, so that patient and/or organ movement arising during the computer tomography examination can be immediately visually perceived.

4 Claims, 2 Drawing Sheets

COMPUTER TOMOGRAPHY APPARATUS HAVING MEANS FOR PRODUCING A SHADOWGRAPH

BACKGROUND OF THE INVENTION

1. Field of the Invention

The present invention is directed to a computer tomography apparatus, and in particular to such a computer tomography apparatus having the capability of preparing x-ray shadowgraphs.

2. Description of the Prior Art

Computer tomography systems are known in the art which have the capability of producing one or more x-ray shadowgraphs of an examination subject, in order to define the examination region before conducting the computer-tomographic examination. In such known systems, the patient is usually moved through the measurement opening, with the x-ray focus being held at a fixed angular position, and a shadowgraph, i.e., an x-ray projection image, is produced continuously or pulsed line-by-line. This conventional exposure technique for producing a shadowgraph involves the following problem.

Particularly given a fast scan sequence, known as dynamic CT and spiral CT, the processing speed of image processors, even high-performance CT image processors, is usually not adequate to reconstruct the CT tomograms in steps and to display such tomograms in real time on the monitor. This means that the examining attendant has no immediate visual control over the current exposure execution. The momentary slice position, and possible patient motions during the scan sequence, thus cannot be directly perceived. The shadowgraph obtained prior to conducting the CT examination will not include such image information.

It is known to reconstruct both computer tomograms and shadowgraphs for arbitrary projection directions from the data generated during scanning of a measurement volume, and to reproduce the shadowgraph in real time, as described in German OS 41 03 588.

SUMMARY OF THE INVENTION

It is an object of the present invention to provide a computer tomography apparatus including an image processing system which permits patient and organ motions to be immediately identified, by means of real time shadowgraphs, even during the execution of a spiral CT scan.

The above object is achieved in accordance with the principles of the present invention in a computer tomography apparatus wherein a shadowgraph, referred to herein as a "conventional shadowgraph," is generated prior to conducting a CT examination, and one or more real time shadowgraphs are subsequently generated in real time during an examination. The shadowgraphs are generated by calculations made using data obtained from the CT apparatus. The conventional shadowgraph and the real time shadowgraph are stored and, upon a request from the operator, are supplied to a superimposition stage wherein the two shadowgraphs are additively or subtractively superimposed to obtain a superimposed shadowgraph. The superimposed shadowgraph can be displayed at any time during the CT examination, and, due to the additive or subtractive superimposition of the two shadowgraphs, changes in the patient position, or patient movement, can be easily ascertained from the displayed image.

DESCRIPTION OF THE PREFERRED EMBODIMENTS

Figure 1:
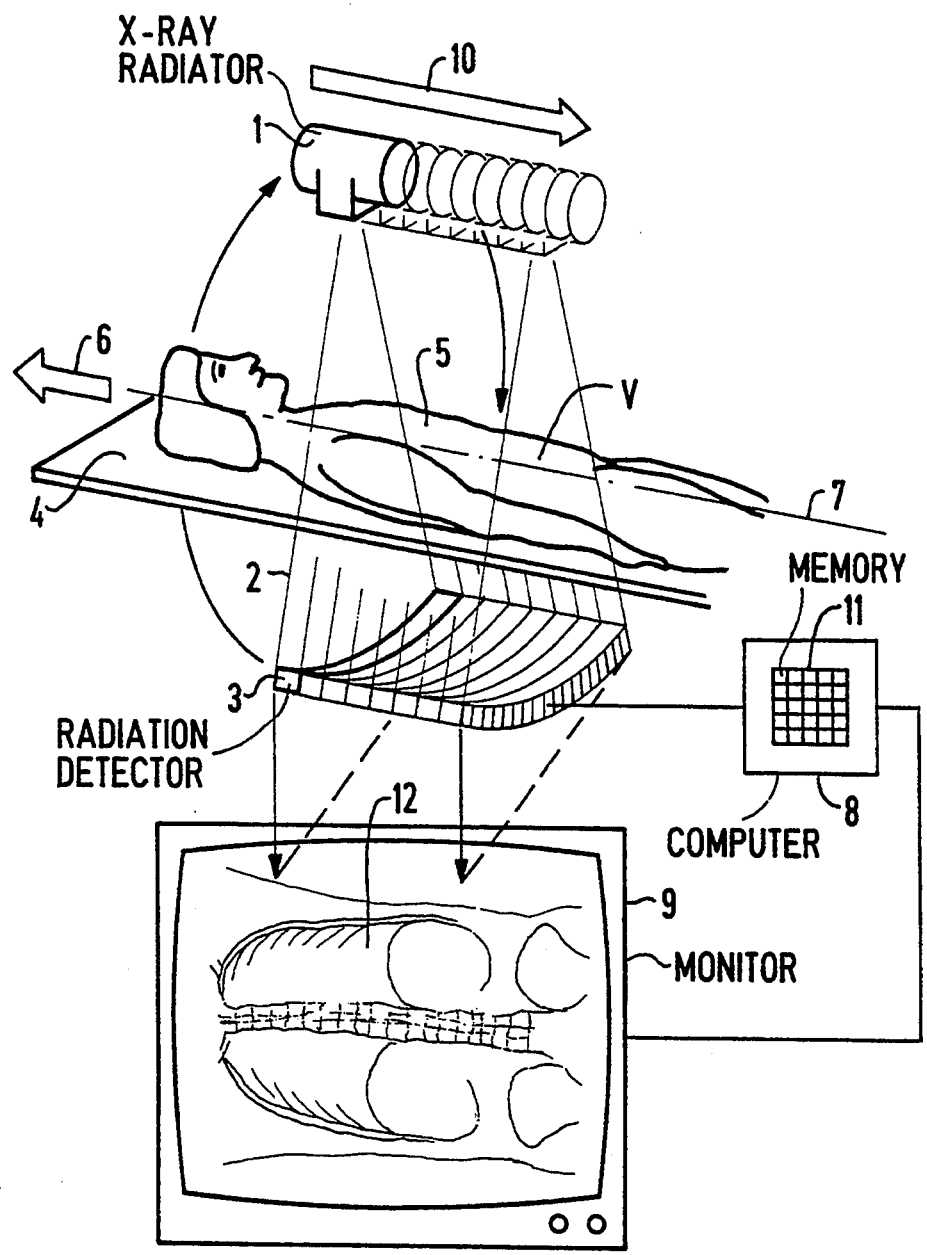
FIG. 1 is a schematic representation of the basic components of a computer tomography apparatus constructed in accordance with the principles of the present invention.

As shown in FIG. 1, a computer tomography apparatus includes an x-ray radiator 1 which emits a fan-shaped x-ray beam 2 which is incident on a radiation detector 3 which is curved around the focus of the x-ray radiator 1. The radiation detector 3 is composed of a row of detector elements. A patient support 4, on which a patient 5 lies, is disposed between the x-ray radiator 1 and the radiation detector 3, so that the x-ray beam 2 penetrates the patient 5.

For scanning a volume of the patient 5, the patient support 4 is adjusted by a defined amount in the direction of the arrow 6, and the measurement unit, consisting of the x-ray radiator 1 and the radiation detector 3, rotates around the system axis 7, as indicated by the curved arrows. The detector elements of the radiation detector 3 generate electrical signals corresponding to the radiation incident thereon, the signals constituting data which are supplied to a computer 8 which calculates images of the patient therefrom and effects reproduction of the calculated images on a display 9. The images calculated from a number of projection directions of the x-ray beam 2 will be computer tomograms of the scanned volume, which an image calculated for a given, single projection direction of the x-ray beam 2 will be a real time shadowgraph of the scanned volume.

Alternatively to adjustment of the patient support 4 in the direction of the arrow 6, the measurement unit can be moved in the direction of the arrow 10 for scanning a predetermined volume of the patient 5, with the patient support 4 at rest.

During the scanning of a defined volume of the patient 5, the data generated by the detector elements of the radiation detector 3 for specific projection directions, namely for specific angular positions of the measurement unit, are intermediately stored in a memory 11 of the computer 8, as described in more detail below. The computer 8 can then calculate a real time shadowgraph of the patient 5 from the data simultaneously with the tomography exposure of the scanned volume of the patient 5, the shadowgraph being reproducible on the display 9. A schematic representation of such a real time shadowgraph is shown on the display on the monitor 9 in FIG. 1 and is referenced 12. This real time shadowgraph is for volume V of the patient 5 which was scanned in the embodiment of FIG. 1.

As a consequence of the fact that only a specific projection from a rotational scanning of the measurement system is used for the calculation of a real time shadowgraph, it does not matter whether the CT exposures are undertaken using a step-by-step feed of the patient support 4, or using a continuous feed of the patient support 4 (or step-by-step or continuous movement of the x-ray radiator 1 ). The presentation of the real time shadowgraph is basically suited for all CT operating modes wherein relative motion between the patient support 4 and the x-ray radiator 1 is produced.

The measurement system consisting of the x-ray radiator 1 and the radiation detector 3 can be locked in position to prevent rotation thereof, so that a shadowgraph on the basis of a relative displacement of the locked measurement system with reference to the patient support 4 in the longitudinal direction can be produced, in addition to the real time shadowgraph. Such a shadowgraph with the measurement system in the lock position corresponds to the type of shadowgraph which is obtained in known systems prior to conducting the CT examination, and thus will be referred to as a "conventional shadowgraph." By means of additive or subtractive image superimposition of the real time shadowgraph with the conventional shadowgraph registered at the beginning of the examination, patient movement and organ movements can be identified immediately during the CT scan.

Figure 2:
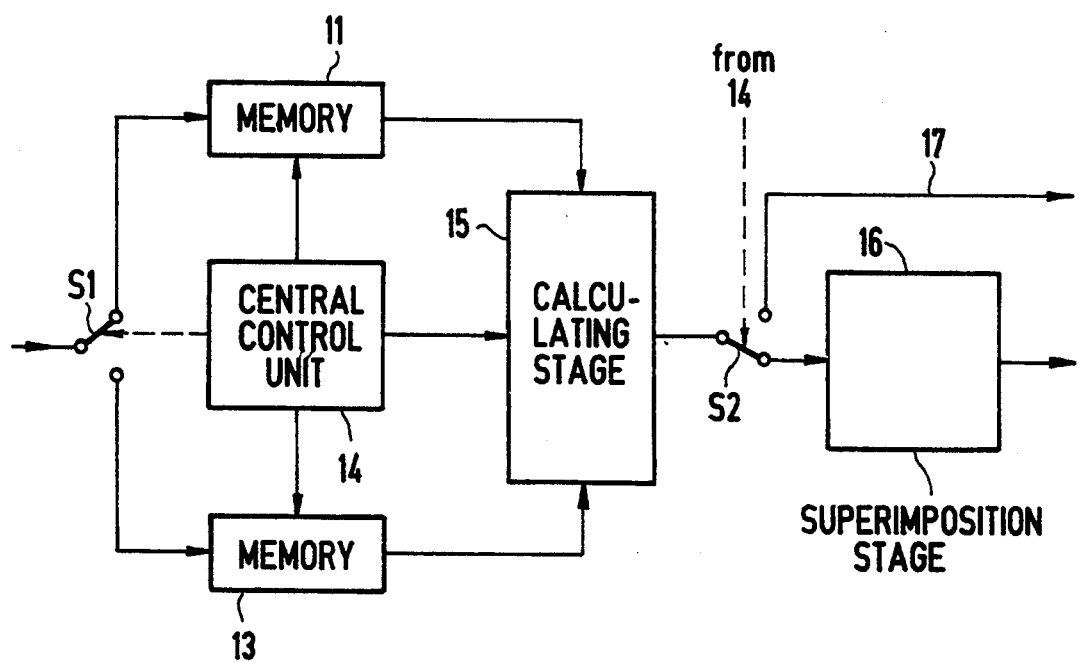
FIG. 2 is a schematic block diagram showing the components for producing the superimposed image.

An exemplary embodiment for obtaining such a superimposed image is shown in FIG. 2.

Within the computer 8, the signals from the detectors 3 are supplied either to the memory 11 or to a memory 13 via a switch S1 under the control of a central control unit 14. The state of the switch S1 will depend on the mode of operation of the apparatus. Prior to beginning a computer tomography scan, for example, the data for the aforementioned conventional shadowgraph can be obtained and stored in the memory. 13. During a tomography scanning mode, the central control unit 14 can change the state of the switch S1 so that the data from the detector 3, for generating the aforementioned real time shadowgraph, are supplied to the memory 11. This takes place simultaneously with the supply of data to the computer 8 for constructing the computer tomograph. The tomographic data supply can take place in parallel with the shadowgraph data supply along a conventional path not shown in FIG. 2. Alternatively, the switch S1 may have a third pole connected directly to the calculating unit 15, the switch S1 then being operated in a multiplexed manner by the central control unit 14.

Data are supplied from the memories 11 and 13 at separate times, under the control of the central control unit 14, to the calculating stage 15, wherein the conventional shadowgraph and the real time shadowgraphs are separately generated. Also under the control of the central control unit 14, the calculating stage 15 forwards the conventional shadowgraph and the real time shadowgraph to a superimposition unit 16, wherein an additive or subtractive superimposition of the two shadowgraphs is made. As a result of the superimposition of the conventional shadowgraph, made at the beginning of the exposure, with the real time shadowgraph made during the collection of data for the tomographic image, changes in the patient position, and other image-related information, can be immediately perceived upon portrayal of the superimposed images on the monitor 9. If the conventional shadowgraph or the real time shadowgraph is desired to be portrayed by itself on the monitor 9, this can be accomplished by operating a switch S2, also controlled by the central control unit 14, so that the output of the calculating stage 15 is supplied to a direct output line 17, which bypasses the superimposition unit 16 and leads directly to the monitor 9. The switch S2 and the direct output line 17 can be avoided by the central control unit 14 instructing the calculating stage 15 to generate a digital image consisting completely of zeros or, depending on the desired contrast, consisting completely of ones, so that the desired image (i.e., either the conventional shadowgraph or the real time shadowgraph) is "superimposed" in the superimposition unit 16 with this "empty" image.

The image dose available for the real time shadowgraph is substantially below the image dose which is necessary for a conventional shadowgraph which is generated with the measurement system being locked. For an anatomical orientation in the real time shadowgraph, however, the presentation of high-contrast objects (bones, lung, etc. ) using the lower dose is usually sufficient for an adequate contrast.

The noise component in the image can be further reduced without a noticeable decrease in the topical resolution by summation of the data supplied to the memory 11 over two or more immediately successive real time projections.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computer tomography apparatus comprising:
   a rotatable measuring unit for generating tomographic data in a scan of a subject by irradiating said subject with x-rays from a plurality of different projection directions;
   memory means for storing a data set obtained prior to said scan by irradiating said subject from one projection direction with said measurement unit in a locked position;
   memory means for storing a second data set obtained in real time during said scan by irradiating said subject from at least one projection direction;
   means for calculating a first shadowgraph of said subject from said first data set and for calculating a second, real time shadowgraph of said subject from said second data set;
   means for superimposing said first and second shadowgraphs to obtain a superimposed shadowgraph; and
   means for visually displaying said superimposed shadowgraph during said scan.

2. A computer tomography apparatus as claimed in claim 1 wherein said measurement unit assumes a selected projection direction a plurality of times during said scan, and wherein said memory means for storing said second data set comprises memory means for storing a second data set obtained in real time during said scan from a summation of data obtained with said measurement unit at said selected projection angle for at least two times.

3. A computer tomography apparatus as claimed in claim 1 wherein said means for superimposing said first and second shadowgraphs comprises means for additively superimposing said first and second shadowgraphs.

4. A computer tomography apparatus as claimed in claim 1 wherein said means for superimposing said first and second shadowgraphs comprises means for subtractively superimposing said first and second shadowgraphs.

* * * * *